United States Patent [19]

Levine et al.

[11] 4,324,672
[45] Apr. 13, 1982

[54] DISPERSANT ALKENYLSUCCINIMIDES CONTAINING OXY-REDUCED MOLYBDENUM AND LUBRICANTS CONTAINING SAME

[75] Inventors: Stephen A. Levine; Raymond C. Schlicht, both of Fishkill; Harry Chafetz, Poughkeepsie, all of N.Y.

[73] Assignee: Texaco, Inc., White Plains, N.Y.

[21] Appl. No.: 162,709

[22] Filed: Jun. 25, 1980

[51] Int. Cl.$^3$ .............................................. C10M 1/54
[52] U.S. Cl. .................................. 252/49.7; 252/46.4; 252/400 R
[58] Field of Search .................. 252/46.4, 49.7, 400 R

[56] References Cited

U.S. PATENT DOCUMENTS

| | | | |
|---|---|---|---|
| 2,753,306 | 7/1956 | Fields | 252/46.4 |
| 2,758,089 | 8/1956 | Hoff et al. | 252/46.4 |
| 2,866,732 | 12/1958 | Hoff et al. | 252/46.4 X |
| 3,223,625 | 12/1965 | Cyphers et al. | 252/49.7 X |
| 3,281,355 | 10/1966 | Cyphers et al. | 252/46.4 |
| 3,290,245 | 12/1966 | Elliott et al. | 252/49.7 X |
| 3,541,014 | 11/1970 | Le Suer | 252/49.7 X |
| 3,652,616 | 3/1972 | Watson et al. | 252/49.7 X |
| 4,176,074 | 11/1979 | Coupland et al. | 252/49.7 X |

FOREIGN PATENT DOCUMENTS

| | | | |
|---|---|---|---|
| 1085903 | 10/1967 | United Kingdom | 252/49.7 |
| 2037317 | 7/1980 | United Kingdom | 252/49.7 |

OTHER PUBLICATIONS

"Advanced Inorganic Chemistry", 2nd Edition, F. A. Cotton et al., p. 947.

*Primary Examiner*—Andrew Metz
*Attorney, Agent, or Firm*—Carl G. Ries; Robert A. Kulason; Henry W. Archer

[57] ABSTRACT

Disclosed are molybdenum derivatives of high molecular weight alkenylsuccinimides and lubricant compositions containing such derivatives which impart dispersant, oxidation inhibition, anti-wear and friction-reducing properties to these compositions.

4 Claims, No Drawings

DISPERSANT ALKENYLSUCCINIMIDES CONTAINING OXY-REDUCED MOLYBDENUM AND LUBRICANTS CONTAINING SAME

BACKGROUND OF THE INVENTION

1. Field of the Invention

The invention relates to the preparation and use of novel molybdenum additives serving to impart dispersant, anti-wear, oxidation-inhibition and friction reducing properties to lubricating compositions. The additives are molybdenum derivatives of high molecular weight alkenylsuccinimides, particularly polyisobutenylsuccinimides or polyalkenylpolyamines which have sludge dispersant properties of their own.

There are numerous patents on the preparation and use in lubricating oils of molybdenum derivatives of organic compounds. This background disclosure is restricted to those which are believed most relevant.

Very basic is U.S. Pat. No. 4,093,614 which discloses double complex salts of alkylene polyamines and various metals one of which can be molybdenum which impart detergency and anti-wear properties to lubricant compositions.

U.S. Pat. No. 3,223,625 is pertinent for disclosing oil soluble colloidal complexes of molybdenum with dispersants including the condensation products alkenylsuccinic anhydrides and polyamines, and the condensation products of alkenylsuccinic anhydrides polyamines and carboxylic acids, these products having residual amino groups to impart basicity. The complexes are prepared by extracting a solution of a hexavalent compound of molybdenum in dilute hydrochloric acid with ethyl ether and heating the extract with the condensation products, followed by vacuum or inert gas blowing.

U.S. Pat. Nos. 4,176,073 and 4,176,074 also relate to molybdenum compounds of interest.

As will be seen hereinafter, none of these suggest in any manner applicants' novel compositions.

SUMMARY OF THE INVENTION

The invention provides an additive having utility in lubricants as an oxidation-inhibitor, anti-wear, dispersant, and friction reducing agent consisting essentially of the reaction product obtained by treating (1) a trivalent to hexavalent, salt or oxide of molybdenum with (2) a coreactant and then with (3) a high molecular weight dispersant hydrocarbyl succinimide.

Lubricating compositions according to the present invention contain at least one additive as above defined in an amount sufficient to provide from 0.01 to 1.0 percent by weight of molybdenum in a fully formulated lubricating oil.

The preparation of the reaction product used in a lubricating composition according to the invention is relatively uncomplicated and can be economically conducted.

The reaction entails treating an oxide or salt of molybdenum with from 15:1 to 1:15 equivalents of a coreactant such as $H_2O_2$ or $SO_2$ and then with the hydrocarbyl succinimide. The ratio of molybdenum to active nitrogen is not critical. In one embodiment, a molybdenum oxide or salt is treated with concentrated hydrogen peroxide under an inert atmosphere at a temperature below about 40° C. After stirring the reaction mixture for about one hour, water is added and the temperature is raised. The mixture is then heated also under an inert atmosphere with the alkenylsuccinimide.

In another embodiment of the invention, a slurry of molybdenum trioxide in water is treated with twice the stoichiometric amount of $SO_2$ to give a mixture of liquid and precipitate, which is slurried in a solvent and heated with an alkenylsuccinimide and the product is recovered under vacuum.

Any salt or oxide of molybdenum having a valence 3 to 6 may be employed as the molybdenum source in the practice of this invention. Such compounds include molybdic acid, ammonium molybdate, sodium molybdate, potassium molybdate and other alkali metal molybdates.

The hydrocarbyl succinimides used have the formula:

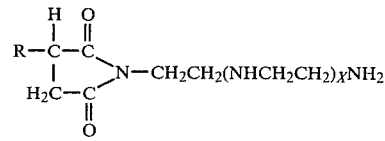

wherein R is an alkenyl radical having from 50 to 200 carbon atoms in the chain, and X is 0 to 10. Preferably, R is polyisobutylene having a molecular weight of about 800 to 1500 and X is 2 or 3. These may be prepared as described in U.S. Pat. No. 3,172,892.

The invention is further illustrated by, but not limited to, the following examples which are representative of its best mode.

EXAMPLE 1

To a flask containing 68.9 g. (0.56 mole) of ammonium molybdate under a nitrogen blanket was added 22.7 (0.20 mole) of 30% hydrogen peroxide over a ten minute period during which time the contents turned yellow. An ice bath was used to maintain the temperature below 41° C. The slurry was stirred for 30 minutes at ambient temperature (ca.26° C.), then 20 ml. of water was added and it was heated to 80° C. Rapid gas evolution was noted. This solution was cooled to ambient temperature and then was added over a 14-minute period to a flask containing 1440 g. (0.26 mole) of alkenylsuccinimide, which had been heated to 80° C. under a nitrogen blanket. The mixture was then heated to 110° C., while a nitrogen purge (100 ml./min.) was employed to sweep out any volatile matter. The contents were held at 110° C. for two hours. The product was diluted with toluene, filtered, and the toluene was stripped off at 80° C., 16 mm Hg. The product was a dark green liquid (1413 g.) containing 1.81 percent molybdenum (68.3% of theory based on Mo charged).

EXAMPLE 2

To a flask containing 56.1 g (0.39 moles) of molybdenum trioxide under a nitrogen blanket was added 22.7 g. (0.20 mole) of 30% hydrogen peroxide over a 10-minute period at 27°–22° C. A thick slurry formed and no color change was observed. It was stirred at 22°–30° C. for one hour, during which time the mixture thickened further and more foam was observed, and 20 ml. of water was added. During the second hour of stirring (30°–31° C.) additional water (30 ml.) was added to thin the mixture, gases were observed evolving, and the color gradually changed from light green to yellow. Then it was heated at 40° C. for an hour during which time an additional 40 ml. of water was added, the color became orange, and more gas evolution was observed. The temperature of the mixture was then raised to 80° C. and the heater was turned off. The product at this point appeared to be an orange liquid above a white solid. The product was allowed to cool to 23° C. and then 3 drops of concentrated sulfuric acid and 10% (v/v) of bis-(2-methoxyethyl) ether were added two hours apart. In a second vessel 1440 g. (0.26 moles) of an alkenylsuccinimide and 100 ml. toluene were mixed under a nitrogen blanket. To this was added the slurried contents of the first vessel and an exotherm of 10° C. was observed. The contents of the second vessel were heated to 120° C. over a 90 minute span during which time a nitrogen purge was started to help strip out the water; the contents of the flask turned a dark green color. The contents were kept at 120° C. for two hours, heated to 190° C. and held there for 10 minutes. The product was filtered at 100° C. The filtrate, an amber liquid (1333 g.), contains 2.04% molybdenum (72.7% of theory based on Mo charged.).

EXAMPLE 3

A slurry was made of 56.1 g. (0.39 moles) of molybdenum trioxide in 200 ml. of water. The slurry was treated with one 25 g. (0.39 mole) portion of sulfur dioxide at 632° C. for 2½ hours. Then another 200 ml. of water was added and the mixture was treated with another 25 g. (0.39 mole) portion of sulfur dioxide at 38°–49° C. for 4 hours. The product consisted of a blue liquid (387 g.) and a bluish grey solid (53 g.). The solid was slurried in 100 ml. of toluene and one-half of the blue liquid. This was added to 1440 g. (0.26 mole) alkenylsuccinimide followed by the remaining blue liquid. A small exotherm (3° C.) was noted. The reactants were then heated to 120° C.; the heavier condensed overhead vapors were taken off (395 ml.) first and then the less dense liquids (85 ml.). The product gradually turned dark green during this period. After heating for two hours at 120°–122° C. a vacuum (22 mm. Hg) was applied for ten minutes to strip out any remaining volatiles. The product (1500 g.) was diluted with toluene, filtered, and stripped at 100° C., at aspirator vacuum, then for two hours at 100° C., 0.9–1.4 mm Hg. The product (1416 g.) was a clear green liquid analyzed as containing 1.89% Mo. 0.92%N, and 0.84%S.

The products of the above examples were blended into motor oil compositions and tested by various tests to evaluate their effectiveness therein. Of these the Bench L-38 Test simulates the engine test environment of Method No. 791a, Method 3405.1, and provides a method for studying the copper-lead bearing corrosion characteristics of crankcase oils. In carrying out this test, a journal bearing is rotated in a journal bearing rig (JBR), which contains a preweighed connecting rod bearing along with 500 ml of test oil. The oil is heated to 200° F. and the journal rotated at 1725 RPM for 2 hours, an activator is added and the temperature increased to 305° F. for 22 hours. The bearings are then removed, cleaned with pentane and reweighed. The difference in weight is then reported as the Bearing Wt. Loss (BWL) in mg.

The activator is prepared by grinding 2 g of lead chloride with a motorized mortar and pestle and 5 ml. of test oil until a paste forms. An additional 25 ml. of test oil is added and the mixture is ground for 5 minutes. The mixture is then transferred to a beaker using approximately 70 ml. of pentane. The mixture is then added to the JBR using pentane in the transfer. The test duration is 24 hours, the air flow rate is 1480 ml/minute.

The Copper Strip Test is based on ASTM Method D-130 and involves immersing a polished copper strip in a given quantity of neat oils containing the additive under test and heating for a temperature and time characteristic of the material being tested. At the end of this period the copper strip is removed, washed and compared with the ASTM Copper Strip Corrosion Standards.

The Bench IIID Test measures the oil thickening tendencies of motor oils under high temperature conditions. The test consists of oxidizing a sample of oil in the presence of air with an iron and copper catalyst at 340° F. After 24, 48 and 72 hours the percent increases in viscosity at 40° C. and the evaporation loss (in milliliters) are determined on the oxidized oil. After 24 and 48 hours, fresh make-up oil is added to the oxidized oil.

TABLE I

| EVALUATION OF MOLYBDENUM CONTAINING SUCCINIMIDES | | | | | |
|---|---|---|---|---|---|
| | Ref. A[1] | Ref. B[2] | Example 1 | Example 2 | Example 3 |
| Composition, % | | | | | |
| Alkenyl dispersant | 3.00 | 3.00 | — | — | — |
| Mo Dispersant | — | — | 3.00 | 3.00 | 3.00 |
| ZDDP, % Zn* | 0.10 | 0.05 | 0.05 | 0.05 | 0.05 |
| Base Blend** | 96.63 | 97 | 97 | 97 | 97 |
| Molybdenum, % | — | — | 0.05 | 0.02 | 0.05 |
| Dispersancy Data | 4.0 | 3.5 | 2.0 | 3.0 | 4.0 |
| Cu Corr., 3hr./300° F. | | 1B | 1B | 1A | 1A |
| Oxidation[3], 48 hr. | 4.5 | 193 | 22.3 | 39.8 | 35.3 |
| 72 hours | 20 | TVTM[5] | 39.0 | 54.7 | 56.2 |
| Cu-Pb Bearing, BWL[4] | 15.7 | | — | 33.1 | 31.9 |
| 4-Ball Wear, mm scar diam 1hr./1800 rpm/200° F./40 Kg | 0.46 | 0.51 | 0.52 | 0.38 | 0.36 |

*ZDDP = Zinc dialkyldithiophosphate, a component of the base blend.
**Base blend contains detergent, ashless antioxidant, ZDDP, viscosity index improver, and mineral oil.
[1]Contains twice the zinc by weight of the other blends, the remaining active ingredients are present in the same amount as in the other blends.
[2]Direct reference to the other blends, contains the same ingredients at the same concentrations, except for molybdenum.
[3]Bench IIID Test - data are percent viscosity increase.
[4]Bearing Weight loss, mg.
[5]Too viscous to measure.

The fourth test employed was the Four Ball Wear Test described in U.S. Pat. No. 3,384,588 which measures the amount of wear a lubricating oil permits under engine test conditions with and without additives to be tested. The greater amount of wear, the poorer the ability of the test oil composition to prevent such wear. This wear is measured in terms of millimeter wear scar diameter. This test was run for 1 hour at 1800 rpm/200° F./40 kg load. The friction coefficient was measured at the end of the test when the anti-friction film is fully developed.

In Table I, Blends A and B contain only the starting alkenyl dispersant but no molybdenum and varying amounts of zinc. With each of Examples 1,2, and 3, it is seen that the results of 4-Ball Wear tests are improved. The B-L-38 data are acceptable. The copper-lead bearing corrosion has not been unacceptably degraded, as further shown by the copper strip corrosion test results. Dispersancy also is not degraded.

Table II shows the frictional improvement obtained with the present additives:

TABLE II

| | FRICTIONAL IMPROVEMENTS[1] | | |
|---|---|---|---|
| Examples | 1 | 2 | 3 |
| Ref. Oil, Raw Data (Ft.-lbs. torque) | 2.62 | 3.08 | 3.08 |
| Ref. Oil + Example, Raw Data (Ft.-lbs. torque) | 2.49 | 2.95 | 2.97 |
| % improvement | 5.0 | 4.2 | 3.6 |

[1]Torque required to motor an engine containing the oil under test is measured. The results of this test have been found to correlate with field experience using a large fleet of cars under varied on-the-road driving conditions (% change in torque correlates with % change in fuel economy).

All the oils used in this test are formulated to a constant calculated molybdenum content of 0.08% (w/w).

From their chemical analyses and on the basis of their preparation the additives of the present invention probably have the empirical formula shown below:

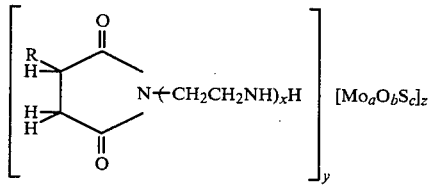

where $x=1$ to 10, $y=1$ to 4, $z=1$ to 5, $a=1$ to 10, $b=0$–4, and $c=0$–4.

The present compositions can also contain a combination of other well known additives in an amount sufficient to achieve each additive's function.

Lubricating compositions according to this invention comprise a major amount of any of the well-known types of oils of lubricating viscosity as suitable base oils. They include hydrocarbon or mineral lubricating oils of naphthenic, paraffinic and mixed naphthenic and paraffinic types. Such oils may be refined by any of the conventional methods such as solvent refining and acid refining. Synthetic hydrocarbon oils of the alkylene polymer type or those derived from coal and shale may also be employed—alkylene oxide polymers and their derivatives—alkylene oxide polymers and their derivatives and esters in which the terminal hydroxyl groups have been modified, are also suitable. Synthetic oils of the dicarboxylic acid ester type including dibutyl adipate, di-2-ethylhexyl sebacate, di-n-hexyl fumaric polymer, dilauryl azelate, and the like may be used. Alkyl benzene types of synthetic oils such as tetradecyl benzene, etc., are also included.

What is claimed is:

1. A composition of matter having oxidation inhibiting, dispersant and friction reducing properties in lubricants consisting essentially of the product obtained by reacting a hexavalent salt or oxide of molybdenum with from 15:1 to 1:15 equivalents of hydrogen peroxide and then with an alkenyl succinimide of the formula:

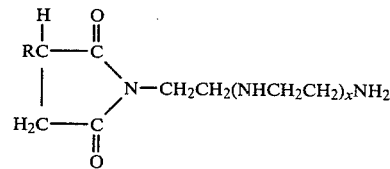

wherein R is an alkenyl radical having from 50 to 200 carbon atoms in the chain and x ranges from 0 to 10.

2. The composition of claim 1, wherein ammonium molybdate is reacted with concentrated hydrogen peroxide under an inert atmosphere, followed by addition of water; heating; further heating under an inert atmosphere with said alkenylsuccinimide; dilution of the resulting product with solvent and vacuum distillation of said product to recover said composition.

3. The composition of claim 1, wherein molybdenum trioxide is reacted with concentrated hydrogen peroxide followed by incremental additions of water to the resulting reaction mass; heating; acidification of said reaction mass; addition of said alkenyl succinimide in an inert solvent; heating and filtering to recover said composition.

4. A lubricant comprising a major amount of an oil of lubricating viscosity and a sufficient amount of the composition of claim 1 to provide from 0.01 to 1.0 percent by weight of molybdenum in said lubricant.

* * * * *